United States Patent [19]

Fujita et al.

[11] 3,999,991
[45] Dec. 28, 1976

[54] THIOINDIOXYL AZO DYE DEVELOPER FOR DIFFUSION TRANSFER PROCESS

[75] Inventors: Shinsaku Fujita; Seiki Sakanoue, both of Minami-ashigara, Japan

[73] Assignee: Fuji Photo Film Co., Ltd., Minami-ashigara, Japan

[22] Filed: Nov. 8, 1974

[21] Appl. No.: 522,152

[30] Foreign Application Priority Data

Nov. 8, 1973 Japan .............. 48-125818

[52] U.S. Cl. .................. 96/73; 96/3; 96/29 D; 96/77; 96/99
[51] Int. Cl.² .............. G03C 7/00; G03C 1/40; G03C 1/76; G03C 1/10
[58] Field of Search ........ 96/3, 29 D, 77, 99, 96/73

[56] References Cited

UNITED STATES PATENTS 3,255,001  6/1966  Blout et al. ............... 96/3
3,307,947  3/1967  Idelson et al. ............. 96/3

Primary Examiner—David Klein
Assistant Examiner—Richard L. Schilling
Attorney, Agent, or Firm—Sughrue, Rothwell, Mion, Zinn & Macpeak

[57] ABSTRACT

A dye developer for silver halide photography comprising both a dye moiety represented by the following general formula (I):

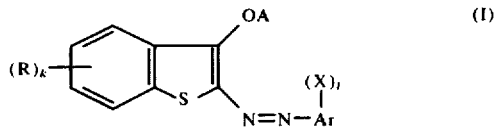

wherein R represents a halogen atom or an alkyl group containing 1 to 4 carbon atoms; $k$ is an integer of from 0 to 4; A represents an acyl group containing 1 to 4 carbon atoms or an alkoxyacyl group containing from 2 to 4 carbon atoms; Ar represents an aromatic nucleus; X represents a halogen atom, an alkyl group, an alkoxy group, an acyl group or an acyloxy group, each containing 1 to 4 carbon atoms and $l$ is an integer of from 0 to 4; and a polyhydric phenol moiety having silver halide developing activity.

22 Claims, 4 Drawing Figures

THIOINDIOXYL AZO DYE DEVELOPER FOR DIFFUSION TRANSFER PROCESS

BACKGROUND OF THE INVENTION

1. Field of the Invention

This invention relates to a dye developer for photography, and particularly to a dye developer used in a photographic material to form an image by the diffusion transfer process. More particularly the present invention relates to a dye developer which at the step of image exposure absorbs light at a short wavelength region so that the spectral sensitivity of the photographic emulsion used in combination therewith is not disturbed, and whose absorption is shifted to a desired, longer wavelength region by reaction with a processing agent.

2. Description of the Prior Art

A diffusion transfer process utilizing a dye developer is well known in the photographic art (for example, as disclosed in U.S. Pat. Nos. 2,983,606, 3,134,764, 3,188,209, 3,255,001, 3,316,090 and 3,345,163).

The dye developer, as noted in U.S. Pat. Nos. 2,983,606, 3,134,764, 3,188,209, 3,255,001, 3,316,090 and 3,345,163, is a compound which contains, in the same molecule, both a group capable of developing a silver halide and a chromophoric system of a dye, and which can be immobilized depending on the amount of silver halide developed, and of which the residual amount can be transferred to an image-receiving layer to form transferred dye images.

The absorption caused by such a dye developer often overlaps the spectrally sensitized region of the photographic emulsion used in combination therewith. Hence the sensitivity of the emulsion is apparently reduced, when the dye developer is incorporated in the sensitized emulsion layer or when the dye developer layer is arranged contiguous to the emulsion layer and in such a manner that image exposure is made through the dye developer layer.

U.S. Pat. Nos. 3,307,947 and 3,579,334 disclose a modified method to eliminate this problem described above. This method employs a dye developer whose absorption is temporarily shifted to a shorter wavelength region and whose desired colored form is restored upon reaction with a processing agent. Unfortunately the same patents disclose magenta color developers. U.S. Pat. No. 3,230,085 also discloses yellow dye developers based on a similar concept, but the carboxylic acid groups of the compounds disclosed in this patent are regenerated by the action of an alkaline material contained in the processing agent, and the presence of the carboxylic acid groups causes an imperfect immobilization of the quinone derivatives formed at the exposed area as the result of reduction of silver ion to silver, thus resulting in a slight "leakage" (transfer of a slight amount of dye) at the highlight area. The "temporary blue shift" i.e., toward a shorter wavelength, of a dye developer described above is generally achieved by the acylation of a hydroxyl or an amino group which is an auxochromic group of an azo dye. An azo dye can exist in either of two tautomeric isomers, the hydrazono form and the azo form. The hydrazono form absorbs longer wavelength light than the azo form, and the acylation is considered to fix the molecule in the azo form, thus achieving the blue shift. Unfortunately, many of the yellow azo dyes exhibiting desirable absorption characteristics such as, for example, pyrazoloneazo, 3-arylazo-2,4-dihydroxyquinoline, 2-arylazo-1,3-indane-dione dyes, etc., cannot be acylated at all or can be acylated only with great difficulty. Further, in the case of pyrazolobenzimidazoleazo or pyrimidazoloneazo dyes, some dyes exhibit only insufficient blue shift upon acylation, or in the case of dyes containing an aniline nucleus, the color of the acylated derivatives is not restored by the processing agent.

Thus there are very few examples of compounds which meet all of the requirements for the present invention, i.e., (1) a desirable absorption as a yellow dye after color restoration; (2) an absorption shift to a sufficiently short wavelength region as a temporary blue shift; (3) rapid color restoration by a processing agent; and (4) perfect inhibition of color restoration during storage of the photographic material. Although the compounds described in Japanese patent application No. 76226/1973 satisfy the above-described requirements fairly well, they still suffer from the shortcomings of poor solubility, low transfer efficiency and particularly unsatisfactory absorption characteristics, i.e., absorption at a too short wavelength region after color restoration, when used in a diffusion transfer material.

SUMMARY OF THE INVENTION

It has now been found that dye developers containing a modified thioindioxyl azo dye moiety have markedly improved properties with respect to solubility, transfer efficiency, and color hue after transfer. The novel azo dye developers of this invention contain both a dye moiety represented by the following formula (I):

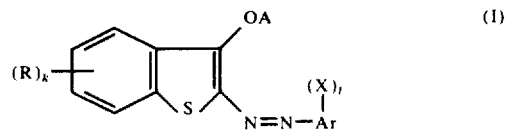

wherein R represents an alkyl group containing from 1 to 4 carbon atoms or a halogen atom; $k$ is an integer of from 0 to 4; A represents an acyl group containing 1 to 4 carbon atoms or an alkoxyacyl group containing from 1 to 4 carbon atoms; Ar represents an aromatic nucleus; X represents an alkyl group, an alkoxy group, aryl group or an aryloxy group, each containing from 1 to 4 carbon atoms, or a halogen atom; and $l$ is an integer of from 0 to 4; and a polyhydric phenol moiety having a silver halide developing activity.

DETAILED DESCRIPTION OF THE INVENTION

Figure 1:
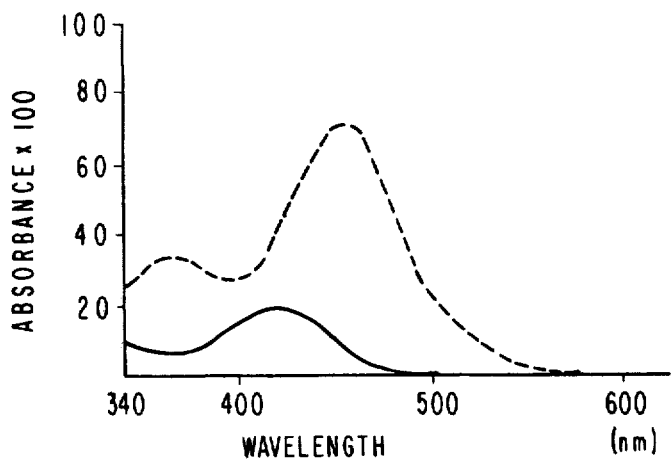
FIG. 1 illustrates the spectral absorption curve of an ethanol solution of Dye Developer No. 1 of this invention and that of the same solution after alkaline treatment followed by neutralization with acetic acid. The solid curve was measured with a solution containing 1.10 mg of Dye Developer No. 1 in 100 ml of ethanol, while the dotted curve was obtained with the same solution after one drop of 1N sodium hydroxide and then one drop of acetic acid were added.

As described above, in the general formula (I) of the dye moiety, R represents a halogen atom such as chlorine, bromine, etc. or an alkyl group containing 1 to 4 carbon atoms such as methyl, ethyl, propyl, iso-propyl, butyl, sec-butyl, t-butyl, etc.; $k$ is 0 to 4; A represents an acyl group containing 1 to 4 carbon atoms such as acetyl, propionyl, butyryl, etc., or an alkoxyacyl group containing 2 to 4 carbon atoms such as methoxyacetyl, etc.; Ar represents an aromatic nucleus such as, benzene, naphthalene, etc.; X represents a halogen atom such as chlorine, bromine, etc., an alkyl group containing 1 to 4 carbon atoms such as methyl, ethyl, propyl, iso-propyl, butyl, sec-butyl, t-butyl, etc., an alkoxy group containing 1 to 4 carbon atoms such as methoxy, ethoxy, propoxy, iso-propoxy, butoxy, sec-butoxy, t-butoxy, etc., an acyl group containing from 1 to 4 carbon atoms such as acetyl, propionyl, butyryl, etc., or an acyloxy group containing 1 to 4 carbon atoms such as acetyloxy, propionyloxy, butyryloxy, etc., and $l$ is 0 to 4.

In the above described general formula of the dye moiety, $k$ is most preferably 0, i.e. no substituents preferably on the benzothiophene ring, for ease of synthesis, however, the substituent, R can be $CH_3$ or the like, considering solubility. When R is a halogen atom, the absorption after transfer slightly shifts to a longer wavelength compared with the case where no substituent is on the ring. Although the most economical group for A is acetyl, a group derived from glycolic acid or a butyric acid group can also be used as A to increase the transfer efficiency for the former or to control the color restoration rate for the latter. When X is an electron attracting atom or group such as a halogen atom or an acetyl group, the spectral absorption after transfer appears at a shorter wavelength region than when no substituents are present on the ring, and when X is an electron donating moiety such as an alkoxy group, a shift to a longer wavelength is observed. However, when X is at the ortho-position to the azo group, a bathochromic shift is always observed whether X is electron attracting or donating.

The polyhydric phenol moiety having silver halide developing activity is preferably a 2,5-, 3,4-, or 2,3-dihydroxyphenyl group which also can be nuclear substituted with alkyl groups containing from 1 to 4 carbon atoms or halogen atoms.

The bond between the dye moiety and the polyhydric phenol moiety may be any divalent group such as an alkylene group containing from 1 to 6 carbon atoms or a $+CH_2\!\!+_{p} Y'+CH_2\!\!+_{q}$ group wherein Y' represents —O—, —S—, —$SO_2$— or —CONH— and $p$ and $q$ each represents an integer of at least 1 and the sum of $p+q$ is 6 or less Alternatively, the dye moiety can be directly linked to the polyhydric phenol moiety.

In a more preferred embodiment, the dye developer of the present invention can be represented by the formula (II):

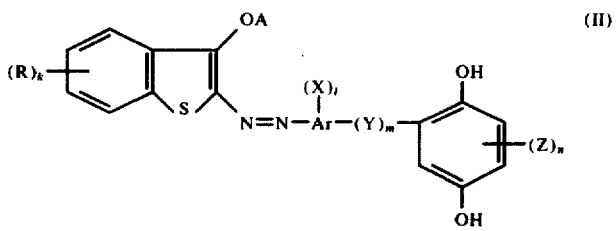

wherein R, $k$, A, Ar, X and $l$ are the same as described in the general formula (I); Y represents an alkylene group containing from 1 to 6 carbon atoms or a $+CH_2\!\!+_{p} Y'+CH_2\!\!+_{q}$ group wherein Y' represents —O—, —S—, —$SO_2$— or —CONH—, and $p$ and $q$ each repesents an integer of at least 1 and the sum of $p+q$ is 6 or less; $m$ is 0 or 1; Z represents an alkyl group containing from 1 to 4 carbon atoms or a halogen atom; and $n$ represents an integer of from 1 to 3.

Specific examples of compounds of the present invention include the following compounds.

1. 3-Acetoxy-2-[m-(hydroquinonylmethyl)-phenylazo]benzo[b]thiophene
2. 3-Butyryloxy-2-[m-(hydroquinonylmethyl)-phenylazo]-5-methylbenzo[b]thiophene
3. 3-Acetoxy-2-[2'-chloro-5'-(hydroquinonylmethyl)phenylazo]benzo[b]thiophene
4. 3-Acetoxy-2-[p-(2'-hydroquinonylethyl)-phenylazo]benzo[b]thiophene
5. 3-Acetoxy-5-chloro-[p-(2'-hydroquinonylethyl)-phenylazo]benzo[b]thiophene
6. 3-Acetoxy-2-[2'-acetoxy-5'-(hydroquinonylmethyl)phenylazo]benzo[b]thiophene
7. 3-Acetoxy-2-[2'-methyl-5'-(hydroquinonylmethyl)phenylazo]benzo[b]thiophene
8. 3-Butyryloxy-2-{m-[2,5-bis(butyryloxy)benzyl]-phenylazo}benzo[b]thiophene The term "hydroquinonyl" group used herein refers to a 2,5-dihydroxylphenyl group.

The dye developer of the present invention can be synthesized using the method of synthesis of U.S. patent application Ser. No. 452,576, filed Mar. 19, 1974. That is, an aromatic primary amine represented by the general formula (III)

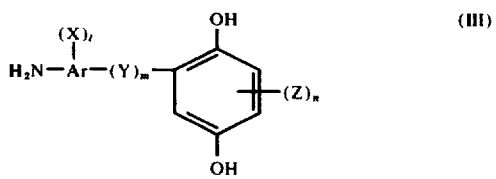

wherein Ar, X, $l$, Y, $m$, Z and $n$ are the same as defined in the general formulae (I) and (II), or a salt thereof, such as a hydrobromide, a hydrochloride, a sulfuric acid salt, a perchloric acid salt or an acetic acid salt, is used as a starting material. Such a compound was found to yield a yellow azo dye having a quinone residue by diazotizing the amine group simultaneously with the oxidation of the hydroquinone group thereof and then coupling the resulting diazonium salt with a thioindoxyl-2-carboxylic acid or a derivative thereof having a nucleus substituent under neutral or acidic conditions as a result of decarboxylation.

The azo dye obtained may be represented by the formula (IV):

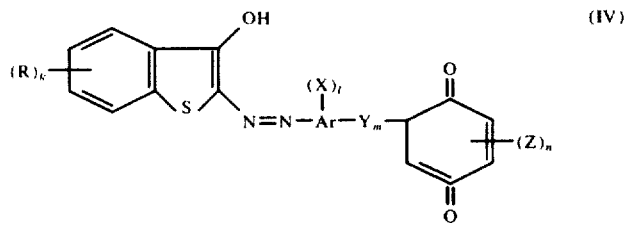

(IV)

wherein R, k, Ar, X, l, Y, m, Z and n are the same as described in general formulae (I) and (II), or by the correspondingg hydrazono structure.

In order for this reaction to occur, an essential condition is that the carboxyl group should be attached to the 2-position of the thioindoxyl nucleus, or else, the coupling reaction must be carried out under alkaline conditions, which, however, causes the once-formed diazonium salt having a quinone residue to decompose, and thus the desired azo dye is not obtained.

An alternative synthetic route for the above-described azo dye (IV) comprises diazotizing an amine having a hydroquinone residue protected by an acetyl group, coupling the resulting product with a thioindoxyl-2-carboxylic acid or with a substituted derivative thereof, removing the protective group to restore the hydroquinone residue, and as a final step, oxidizing the hydroquinone residue of the azo dye. However, the formerly described process is far shorter and simpler, thus having a higher synthetic yield. The dye developer of the present invention can be obtained by acylation of the enolic hydroxyl group of the yellow azo dye (IV) with an acylating agent such as an enol ester (carboxylic acid isopropenyl ester) in the presence of an acid catalyst and then by reduction of the acylated product with 2,5-di-t-butylhydroquinone as described in Japanese patent application No. 42859/1974 or with N,N-disubstituted hydroxylamine as described in U.S. patent application Ser. No. 453,908, filed Mar. 22, 1974, or by hydrogenation of the product using a suitable catalyst such as palladium carbon.

The dye developer of this invention can be used for a photographic material of the type in which the image receiving element is stripped off, for the purpose of viewing from the photographic negative element, and further of the type described in U.S. Pat. Nos. 3,415,644; 3,415,645 and 3,415,646 in which one can view the final image without stripping. Of the various non-stripping type materials, one in which the image is viewed from the side opposite to that on which the exposure was made is especially preferred because no optical means is needed in the camera for inverting the image. In order to achieve desirable color separation, it is essential to arrange layers in the following order; an image receiving layer, a space in which a processing liquid is supplied, a blue sensitive silver halide emulsion layer, and a hydrophilic colloid layer containing a yellow dye developer. It is also essential that image exposure be from the side close to the dye developer containing layer. In such an arrangement, it is significant that the dye developer should assume a temporary structure having an absorption at a short wavelength region.

The dye developer of the present invention can be fixed in the azo form by acylating the azo dye containing a thioindoxyl nucleus, which is shown below in the hydrazono form;

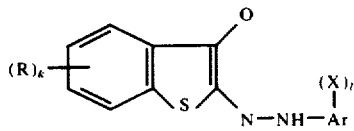

Figure 2:
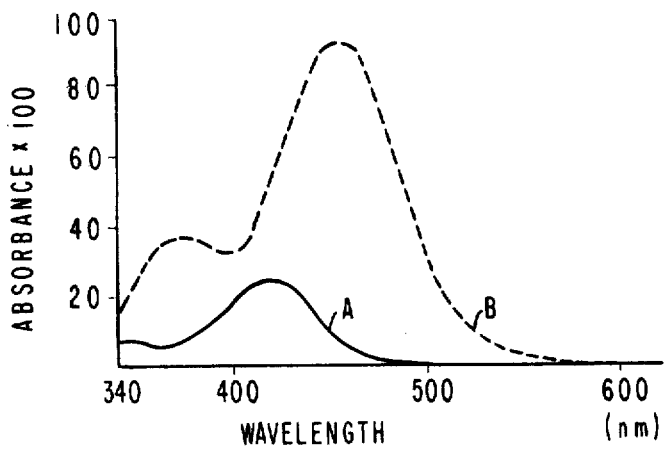
FIG. 2 illustrates the spectral absorption curves of Dye Developer No. 4 of this invention prior to and after alkaline treatment, the solid curve being obtained for a solution containing 1.32 mg of Dye Developer No. 4 in 100 ml of ethanol and the dotted curve for the same solution after one drop of 1N sodium hydroxide was added and then neutralization with acetic acid.

Thus a desirable hypsochromic shift is temporarily achieved. FIGS. 1 and 2 show that the fixation in the azo form by acylation brings about a temporary hypsochromic shift of the dye absorption. The solid curve of FIG. 1 is the spectral absorption curve of Dye Developer No. 1 of the present invention for a concentration of 1.10 mg/100 ml ethanol, and the dotted curve is the spectral absorption curve of the same solution after the addition of a drop of 1N aqueous NaOH followed by neutralization with acetic acid. The two curves of FIG. 2 correspond to the absorption curves of Dye Developer No. 4 for a concentration of 1.32 mg/100 ml methanol, each curve having the same meaning as in FIG. 1. These figures evidently demonstrate the distinctive spectroscopic effect caused by the temporary fixing of the dye in the azo form.

A color photographic element for the diffusion transfer process comprises a silver halide emulsion and a dye developer. An appropriate combination of the spectral sensitivity of the emulsion with the spectral absorption of the resulting dye image is selected depending on the color reproduction desired. For reproduction of natural colors using the subtractive principle, at least two elements must be used, each element comprising an emulsion having a sensitivity only in a limited spectral range and a compound which can form a dye selectively absorbing light in the same spectral range. In particular, photographic elements comprising a blue sensitive silver halide emulsion and a yellow dye forming compound, those comprising a green sensitive emulsion and a magenta dye forming compound and those comprising a red sensitive emulsion and a cyan dye forming compound are quite useful. The silver halide emulsion and the dye developer combined in each photosensitive element can be coated as individual layers in the face to face relationship; or can be admixed in a form of particles thereof to provide a single layer. A preferred multilayer arrangement is, starting from the side of exposure to light, a blue sensitive silver halide emulsion layer, a green sensitive silver halide emulsion layer and then a red sensitive silver halide emulsion layer; and when the emulsions have very high photographic speeds containing silver iodide, a yellow filter layer can preferably be interposed between the blue and green sensitive silver halide emulsion layers. Such a yellow filter layer usually contains one of the following ingredients; yellow colloidal silver dispersion, a dispersed oil-soluble yellow dye, an acid dye mordanted with an alkaline polymeric material, or a basic dye mordanted with an acid polymeric material. It is advantageous for every emulsion layer to be separated from each other by an intermediate layer. The intermediate layer prevents undesirable interaction which might occur between the contiguous emulsion layers having different spectral sensitivities, and comprises a hydrophilic polymer such as, for example, gelatin, polyacrylamide, partially hydrolyzed polyvinyl acetate, or a mixture of a hydrophilic polymer and a hydrophobic polymer latex, as is described in U.S. Pat. No. 3,625,685, which forms a microscopically porous film, or further a polymer such as calcium alginate which is rendered more hydrophilic by the action of the processing agent.

The silver halide emulsions which can be used in the present invention comprise silver chloride, silver bromide, silver chlorobromide, silver iodobromide, silver chloroiodobromide or mixtures thereof, each colloidally dispersed in a hydrophilic medium. The halogen composition is selected depending on the end-use purpose and the processing conditions of the final photographic product. Suitable silver halides are those with an iodide content of from about 1 to 10 mol% and a chloride content not higher than about 30 mol%, the remainder being bromide. The grain size of the silver halide used can be that conventionally employed or fine grains. A preferred range is from about 0.1 to about 2 microns as an average grain size. For certain applications, a narrow grain size distribution is preferred. Cubic, octahedral or mixed crystal forms of the silver halide can be used.

Photographic emulsions containing such silver halide crystals can be prepared by any of the conventionally known methods as are described in P. Glafkides *Chemie Photographique* Second Edition, Chapters 18 to 23, Paul Montel, Paris (1957). Typically, a water soluble silver salt such as silver nitrate and a water soluble halide such as potassium bromide are reacted in the presence of a hydrophilic protective colloid such as gelatin to form a silver halide and then allowed to stand for the crystals to grow in the presence of an excess of halide or of a solvent for the silver halide including ammonium hydroxide. A double or single jet, or a pAg controlled double jet addition process can be employed for the precipitation. Removal of the by-produced water soluble salts from the emulsion can be achieved by water-washing of the chilled gelled emulsion; by dialysis; by water-washing after the addition of a precipitant such as an anionic polymer containing a sulfonate, sulfate ester or carboxylic group or an anionic surface active agent and adjustment of pH; or by water-washing after precipitation of the silver halide emulsion using an acylated protein, as a protective colloid, such as phthaloyl gelatin. Silver halide emulsions for use in the present invention are preferably chemically sensitized by heat-treatment using any of the following sensitizing agents; the naturally occurring sensitizing compounds present in gelatin, a sulfur compound such as sodium thiosulfate, N,N,N'-triethylthiourea, etc., as disclosed in U.S. Pat. Nos. 1,574,944, 2,278,947, 2,410,689, 3,189,458, 3,501,313, a gold compound such as the thiocyanate complex salt or the thiosulfate complex salt of monovalent gold ion as disclosed in U.S. Pat. No. 2,399,083, etc., a reducing agent such as stannous chloride, hexamethylenetetramine, etc., as disclosed in U.S. Pat. Nos. 2,487,850, 2,518,698, 2,512,925, 2,521,926, 2,419,973, 2,419,975, etc. For the present invention, emulsions which tend to form a latent image on the crystal surface as well as those which form a latent image in the interior of the crystal as described in U.S. Pat. Nos. 2,592,550 and 3,206,313, etc. can be suitably employed. A suitable coating amount of the emulsion ranges from about 0.1 $g/m^2$ to 10 $g/m^2$, preferably 0.3 $g/m^2$ to 4 $g/m^2$ (as silver per $m^2$ of the support).

Silver halide emulsions for the present invention can be stabilized using any of the following additives; 4-hydroxy-6-methyl-1,3,3a,7-tetrazaindene, 5-nitroimidazole, 1-phenyl-5-mercaptotetrazole, 8-chloromercurylquinoline, benzenesulfinic acid, pyrocatechin, 4-methyl-3-sulfoethylthiazolidine-2-thione, 4-phenyl-3-sulfoethylthiazolidine-2-thione, etc. Further inorganic stabilizing additives can be used including cadmium or mercury salts, or complex salts of platinum group elements such as the chloro complex salts of paladium. The emulsions can also contain a sensitizing compound such as polyethylene oxide.

The silver halide emulsions for use in the present invention can have an extended spectral sensitivity, according to the requirements, using spectral sensitizers including cyanine, merocyanine, holopolar cyanine, styryl, hemicyanine, oxonol, hemioxonol dyes, etc. Still further examples of spectral sensitizers are described in P. Glafkides, supra Chapters 35 to 41 and F. M. Hamer *The Cyanine Dyes and Related Compounds* (Interscience). Particularly useful cyanine dyes are those which have an aliphatic group (for example, an alkyl group) substituted in the nitrogen atom in the basic heterocyclic ring, the aliphatic group containing a hydroxyl, carboxyl or sulfo group substituent. Such cyanine dyes are described in, for example, U.S. Pat. Nos. 2,503,776, 3,459,553 and 3,177,210.

The dye developer of the present invention can be dispersed in a hydrophilic colloid generally in the following manner. An organic solvent solution obtained by dissolving the dye developer in a solvent is added into an aqueous solution of the hydrophilic colloid as minute droplets. Where a volatile organic solvent such as ethyl acetate, tetrahydrofuran, methyl ethyl ketone, etc. is employed, the solvent can be removed during the drying of the photographic emulsion layer, or by the methods described in U.S. Pat. Nos. 2,322,027 and 2,801,171. Where a solvent miscible with water such as dimethylformamide, 2-methoxyethanol, etc., is used, the solvent can be removed by the methods disclosed in U.S. Pat. Nos. 2,949,360 and 3,396,027, i.e., by washing with water. However, in order to achieve a stable dispersion of the dye developer and also to promote the formation of a dye image, it is advantageous to dissolve the dye developer in a solvent which is substantially immiscible with water and has a boiling point above about 200° C at atmospheric pressure. Such solvents include, for example, dibutyl phthalate, tricresyl phosphate, trihexyl phosphate, N,N-diethyllaurylamide, etc. To promote the solubilization of the dye developer, a volatile or water miscible solvent described above can be used in combination as an auxiliary solvent.

In addition, in place of or in addition to these high boiling point solvents, an oleophilic polymer can be used. Generally, a colloid mill, a high pressure homogenizer, a supersonic emulsifier, etc., can be used for production of a minute dispersion of small droplets. Anionic surface active agents are mainly employed as an emulsifying agent. A suitable amount of the dye developer of this invention ranges from about 0.1 g/m$^2$ to 10 m/g$^2$, preferably 0.3 g/m$^2$ to 4 g/m$^2$ of the support.

The photographic element described hereinbefore in detail is usually superimposed in face-to-face contact with a receiving element which will be explained herein below and processed by spreading an alkaline processing liquid which will also be explained hereinbelow between these elements. The receiving element can be stripped off after transfer, or the image can be viewed without stripping by utilizing a transparent support for the image receiving layer and providing a light reflective layer e.g., a layer containing titanium dioxide between the image receiving layer and the phtotgraphic layer as disclosed in U.S. Pat. No. 3,415,645. Such a light reflective layer can be pre-formed or formed on spreading the alkaline processing liquid which includes a light reflective agent.

The image receiving element essentially includes a mordant layer containing poly-4-vinylpyridine latex (particularly dispersed in polyvinyl alcohol), polyvinyl pyrolidone or a polymer having a quaternary ammonium salt structure as disclosed in U.S. Pat. No. 3,239,337, and, in addition, preferably should have the function of neutralizing the alkaline material from the processing liquid. The processing agent has an alkalinity as high as a pH of about 10 to 11 or higher to promote the image forming process which comprises development of the silver halide emulsion and diffusion of the dye developer. After the formation of the diffusion transfer image has been substantially completed, the pH within the film unit is reduced to about neutrality, i.e., below about 9, more preferably below 8, to inhibit further image formation and to prevent the change of the image gradation during storage as well as deterioration of colors and staining of the highlight area caused by strongly alkaline conditions. For neutralization, a neutralizing layer which contains an acid material in an area density of more than the equivalent of the alkaline material of the processing agent spread over the unit areas is advantageously provided in the film unit. Suitable acid materials are those having an acid group with a pK$_a$ of less than about 9, (especially a carboxyl or sulfonic acid group, or a group which can be converted upon hydrolysis into an acid group) and more particularly a higher aliphatic acid such as oleic acid as is described in U.S. Pat. No. 2,983,606, a polymer comprising an acid monomer such as acrylic acid, methacrylic acid or maleic acid, a partially esterified product derived from such a polymer as described in U.S. Pat. No. 3,362,819, and an acid anhydride. Specific examples of polymeric acid compounds include copolymers of maleic anhydride or the half butyl ester of maleic acid with vinyl monomers such as ethylene, vinyl acetate, vinylmethylether, etc., copolymers of butyl acrylate with acrylic acid, cellulose acetate hydrogen phthalate, etc. A neutralizing layer can contain, in addition to the acid component, cellulose nitrate or polyvinyl acetate; further the neutralizing layer can contain a plasticizer as is described in U.S. Pat. No. 3,557,237. The neutralizing layer can be crosslinked with a polyfunctional aziridine compound or an epoxide compound. This layer can be present in either the image receiving element or the light sensitive element. Most preferably, the neutralizing layer is located between the support of the image receiving element and the image receiving layer. As is disclosed in German Offenlegunsschrift No. 2,038,254, an acid material can be incorporated in the film unit in the form of microcapsules.

The neutralizing layer, i.e., acid containing layer, for use in the present invention is preferably isolated from the processing liquid layer, when it is spread, by a neutralizing rate controlling layer provided therebetween. This netralizing rate controlling layer retards the rate of neutralization and prevents a too rapid, undesirable reduction of the pH of the processing liquid before completion of silver halide development and also of the diffusion transfer which follows.

In a preferred embodiment of the present invention, the image receiving element comprises a support, a neutralizing layer, a neutralizing rate controlling layer, and a mordant layer arranged in this order. The neutralizing rate controlling layer mainly comprises a polymer such as gelatin, polyvinyl alcohol, polyvinylpropylether, polyacrylamide, hydroxpropylmethylcellulose, isopropylcellulose, polyvinylbutyral, partially hydrolyzed polyvinyl acetate, a β-hydroxyethyl methacrylate/ethyl acrylate copolymer, etc. Such a polymer is advantageously crosslinked using an aldehyde such as formaldehyde or using an N-methylol compound. The layer thickness of the neutralizing rate controlling layer is preferably about 2 to 20 microns.

The processing agent used in the present invention is a liquid containing the essential processing ingredients for the development of the silver halide emulsion and the formation of a diffusion transferred dye image; the main solvent is water and the liquid can also contain a hydrophilic solvent such as methanol, 2-methoxyethanol. The processing agent includes an alkaline material in an amount sufficient to maintain the pH required for the development of the emulsion to take place and to neutralize the acid generated during the development and the dye image forming procedure (for example, hydrogen halides such as hydrogen bromide, or carboxylic acids such as acetic acid). Suitable alkaline materials include alkali metal or alkaline earth metal salts or amine compounds such as lithium hydroxide, sodium hydroxide, potassium hydroxide, a calcium hydroxide dispersion, tetramethylammonium hydroxide, sodium carbonate, trisodium phosphate, diethylamine, etc. Most preferably, a very strong alkali is used at a concentration such that the pH is maintained above about 12, more advantageously above 14 at room temperature (about 20° to 30° C). The processing agent further includes a high molecular weight hydrophilic polymer such as polyvinyl alcohol, hydroxyethylcellulose, sodium carboxymethylcellulose, which provides a viscosity ranging from about 1 to 1000 poises (preferably 500 to 600 poises) at room temperature suitable for uniform spreading over the layer to be processed, and which, after concentration due to migration of the water based solvent into the photographic element and the image receiving element, forms a non-flowing film, thus providing a unification of the film unit. This polymer film can also serve to prevent image degradation during storage by suppressing further migration of colored substances into the image receiving layer after substantial completion of the the formation of the diffusion transfer dye image. In some cases the processing agent further includes a light absorptive material such as carbon black or a desensitizing agent as is disclosed in U.S. Pat. No. 3,579,333, in order to prevent fogging of the silver halide emulsion layer by external light during processing.

In the case of the diffusion transfer color process, development processing in the presence of a diffusible onium compound is desirable. Suitable onium compounds include quaternary ammonium, phosphonium or sulfonium compounds. Particularly useful onium compounds include 1-benzyl-2-picolinium bromide, 1-(3-bromopropyl)-2-picolinium-p-toluene sulfonic acid, 1-phenethyl-2-picolinium bromide, 2,4-dimethyl-1-phenethylpyridinium bromide, α-picoline-β-naphthoylmethylbromide, N,N-diethylpiperidinium bromide, phenethylphosphonium bromide, dodecyldimethylsulfonium p-toluene sulfonate, etc. The onium compound should desirably be present in the alkaline processing agent at a concentration of from about 2 to 15% by weight of the weight of the total agent. The presence of the onium compound at processing remarkably improves the quality of the transferred image. Other examples of onium compounds than those illustrated above are described in detail in U.S. Pat. Nos. 3,411,904 and 3,173,786. The processing agent can further contain a development inhibitor such as benzotriazole.

The following examples are given to further explain the synthesis and application to photographic materials of the compounds of the present invention. Unless otherwise indicated herein, all parts, percents, ratios and the like are by weight.

SYNTHESIS EXAMPLE 1

Synthesis of Dye Developer No. 1 a. Synthesis of 2,5-Dimethoxy-3'-nitrobenzophenone

In 1.6 l of methylene chloride was dissolved 280 g of p-dimethoxybenzene and 372 g of m-nitrobenzoyl chloride. In this solution 300 g of aluminum chloride was added with stirring. After being allowed to stand overnight, the mixture was poured into ice water and the organic liquid phase was separated. After the methylene chloride was removed by distillation, the residual product was recrystallized from ethanol to obtain 470 g of pale yellow crystals of the subject compound which had a melting point of 98° C.

b. Synthesis of 2,5-Dimethoxy-3'-aminobenzhydrol 100 g of 2,5-Dimethoxy-3'-nitrobenzophenone was dissolved in 1.3 liters of ethanol. With the addition of a 10% palladium on carbon catalyst, the solution was charged in an autoclave, and hydrogenated for 8 hours at 130° C with an initial hydrogen pressure of 100 kg/cm². The filtrate obtained on removal of the catalyst was concentrated to obtain white crystals. Filtration and air drying provided 57 g of the subject compound, which had a melting point of 132° to 134° C.

c. Synthesis of 1,4-Dimethoxy-2-(3'-aminobenzyl)benzene

To 300 ml of acetic acid were added 96 g of zinc powder and 50 g of the 2,5-dimethoxy-3'-aminobenzhydrol prepared in (b) then 240 ml of a 35% hydrochloric acid aqueous solution was added dropwise at 80° C. After 30 minutes the same amount of the 35% hydrochloric acid solution was further added. After 2 hours of stirring, the mixture was cooled and the supernatant liquid was separated, to which an aqueous solution of sodium hydroxide was added until the pH became 5. An oily product deposited which was extracted with ethyl acetate and washed with an aqueous solution of sodium bicarbonate. Drying with sodium sulfate followed by distillation under a reduced pressure on an oil bath whereby a distillation fraction boiling in the range 170° to 175° C was collected provided 36 g of crystals with a melting point of 81° to 84° C.

d. Synthesis of 2-(3'-Aminobenzyl)hydroquinone 27 g of 1,4-dimethoxy-2-(3'-aminobenzyl)benzene prepared in (c) was mixed with a 46% hydrobromic acid aqueous solution. The mixture was refluxed on an oil bath for 1 to 2 hours. Since crystals deposited when cooled with ice, the filtration was carried out under cooling. The crystals were dissolved in 200 ml of water, and the resulting solution was neutralized by adding 25 g of sodium acetate. The free amine separated was recrystallized from an ethanol-benzene mixture to obtain 16 g of the subject compound. The melting point was 151° to 152° C.

e. Synthesis of 2-[m-(Quinonylmethyl)phenylhydrazono]-3-oxo-1-thiaindane

A mixture of 8.4 g of 2-(3'-aminobenzyl)hydroquinone prepared in (d), 400 ml of ice water, 27 ml of concentrated hydrochloric acid and 0.6 ml of octyl alcohol was prepared and cooled to 0° C. With stirring 8.4 g of sodium nitrite dissolved in 100 ml of water was added dropwise. After 90 minutes of stirring, 1.0 g of sulfaminic acid and then 47 g of sodium acetate was added. To the resulting diazonium solution was added a mixture comprising 7.5 g of thioindoxyl-2-carboxylic acid dissolved in ethanol and an aqueous sodium hydroxide solution containing 2.0 g NaOH. The separated crystals were filtered by suction and dried. The crystals were then recrystallized from a 1,2-dichloroethaneethyl acetate mixture to obtain 9.4 g of orange crystals of the subject compound with a melting point of 189° to 190° C.

f. Synthesis of 3-Acetoxy-2-[m-(quinonylmethyl)phenylazo]-benzo[b]thiophene

On a steam bath was refluxed a solution prepared by dissolving in 100 ml of 1,2-dichloroethane 9.2 g of the azo dye synthesized in (e), 15 ml of isopropenyl acetate and a catalytic amount (0.3 ml) of concentrated sulfuric acid.

The reacted solution was treated with sodium sulfate and with activated carbon after washing with water. Filtration and concentration caused crystals to deposit, which were separated by filtration and dried in air after washing with ethyl acetate. The subject compound was obtained in an amount of 6.8 g, having a melting point of 190° to 191° C.

g. Synthesis of Dye Developer No. 1

Into 100 ml of 1,2-dichloroethane was dissolved 6.8 g of the acetylated compound prepared in (f). To this solution 5.0 g of 2,5-di-t-butylhydroquinone was added and the mixture was then stirred for 3 hours. The precipitated crystals were filtered out, washed with benzene and air dried. Dye Developer No. 1 thus obtained exhibited a melting point of 201° to 203° C. The yield was 6.4 g.

SYNTHESIS EXAMPLE II

Synthesis of Dye Developer No. 4 a. Synthesis of the Quinone Derivative

In 150 ml of acetone were refluxed 22.5 g of 2-[p-($\beta$-hydroquinonylethyl)phenylhydrazono]-3-oxo-1-thiaindane and 12.5 g p-benzoquinone. The formed crystals were filtered, washed in acetone, and recrystallized from 1,2-dichloroethane to obtain the corresponding quinone derivative in an amount of 19.5 g. The melting point was 176° to 180° C.

b. Acetylation of the Enol

Into 800 ml of 1,2-dichloroethane were dissolved 19.5 g of 2-[p-($\beta$-quinonylethyl)phenylhydrazone]-3-oxo-1-thiaindane obtained in (a), 60 ml of isopropenyl acetate and 1 ml of concentrated sulfuric acid. The resulting solution was refluxed on a steam bath for 1.5 hours, followed by the successive treatments similar to those in Synthesis Example I (b). Recrystallization from 1,2-dichloroethane yielded 12.6 g 3-acetyl-2-[p-($\beta$-quinonylethyl)phenyl-azo]benzo[b]thiophene with a melting point of 193° to 195° C.

c. Synthesis of Dye Developer No. 4

In 500 ml of 1,2-dichloroethane was dissolved 12.0 g of the compound prepared in (b). The reduction was carried out on this solution after the addition of 6.4 g of 2,5di-t-butylhydroquinone in a similar manner as described in Synthesis Example I. Recrystallization three times from acetone provided 6.6 g of Dye Developer No. 4 having a melting point of 226° to 228° C.

EXAMPLE I

Photographic Element (I) was prepared by successively coating the following layers on a cellulose triacetate film having thereon a gelatin subbing layer.

1. Yellow Dye Developer Layer

After 1 part of Dye Developer No. 1 was dissolved in 1 part of N,N-diethyllaurylamide and 4 parts of cyclohexane, the resulting solution was emulsified in an aqueous gelatin solution with the aid of sodium n-dodecylbenzene sulfonate (dispersant). The emulsion was coated in a coating rate of 1.2 g/m² of Dye Developer 1, 2.4 g/m² of gelatin and 0.7 g/m² of N,N-diethyllaurylamide.

2. Blue Sensitive Emulsion Layer

A blue sensitive silver iodobromide (containing 2 mol% silver iodide) coated at a rate of 3.5 g/m² of silver, and 4.0 g/m² of gelatin.

3. Protective Layer

A solution prepared by dissolving 1 part of 4'-methylphenylhydroquinone in 1 part of tri-o-cresyl phosphate and 1.5 parts of ethyl acetate was emulsified in an aqueous gelatin solution with the aid of sodium n-dodecylbenzene sulfonate. This emulsion was coated at a rate of 0.20 g/m² of 4'-methylphenylhydroquinone, 0.6 g/m² of gelatin, and 0.20 g/m² of tri-o-cresyl phosphate. Mucochloric acid was used as a hardening agent. For the purpose of comparison with Photographic Element (I), Photographic Element (II) was prepared in the same manner as Photographic Element (I) except that the yellow dye developer layer was replaced with the following yellow dye developer layer.

Yellow Dye Developer Layer

A solution was prepared by dissolving 1 part of 1-phenyl-3-(N-n-hexylcarboxyamido)-4-[4-(2-hydroquinonylethyl)phenylazo]-5-pyrazolone (a dye developer for comparison) into 2.5 parts of N,N-diethyllaurylamide and 2.5 parts of cyclohexanone. This solution was emulsified with the aid of sodium n-dodecylbenzene sulfonate in an aqueous gelatin solution. The resulting dispersion was coated at a rate of 1.4 g/m² of the comparison dye developer, 2.4 g/m² of gelatin, and 3.5 g/m² of N,N-diethyllaurylamide.

Next, a polyethylene film support was coated successively with the following layers to form an image receiving element.

1. Acid Polymer Layer

A methyl ethyl ketone solution of the half butyl ester of maleic anhydride and vinyl methyl ether copolymer (1:1 molar ratio) with an average molecular weight of about 100,000, containing 20% of the polymer, was coated in a dried thickness of 20 microns.

2. Neutralizing Rate Controlling Layer

A 7 micron thick coating on a dry basis was provided by coating a solution prepared by dissolving 1 part of 2-hydroxyethyl methacrylate in 3 parts of acetone and 1 part of water.

3. Image Receiving Layer

A solution was prepared by dissolving 1 part of poly-4-vinylpyridine, 2 parts of polyvinyl alcohol (degree of saponification; 98%, degree of polymerization; 1800) and 1/20 part of 1-phenyl-5-mercaptotetrazole into 150 parts of water containing ½ part of glacial acetic acid. This solution was coated in a coating rate of 3.2 g/m² of poly-4-vinylpyridine, 3.2 g/m² of polyvinyl alcohol, and 0.16 g/m² of 1-phenyl-5-mercaptotetrazole.

An exposure of 20 C.M.S. from an incandescent lamp of a color temperature of 2854° K was made from the support side of each of the Photographic Elements (I) and (II) through an optical wedge superimposed thereon. Then the image receiving element was superimposed, and between the two elements the following processing liquid was spread at a rate of 1.5 ml/100 cm² of the image receiving element to cause development and transfer.

| Processing Liquid Composition | |
|---|---|
| Water | 100 ml |
| Potassium Hydroxide | 11.2 g |
| Hydroxyethylcellulose | 4.0 g |
| Benzotriazole | 3.5 g |
| Potassium Thiosulfate | 0.5 g |
| Lithium Nitrate | 0.5 g |
| Zinc Nitrate | 0.5 g |
| N-Benzyl-$\alpha$-picolinium Bromide | 2.3 g |

After about 1 minute of development, the image receiving element was stripped off and then thoroughly washed with water. On the image receiving element was observed a transferred yellow dye image corresponding to the impinged light intensity of exposure.

Measurement of the transmittance optical density due to the transferred yellow dye at the non-exposed area using a blue filter gave a $D_{max} = 1.20$ and a $D_{min} =$ 0.15 for Photographic Element (I) and a $D_{max} = 0.90$ and a $D_{min} = 0.10$ for Photographic Element (II).

Figure 4:
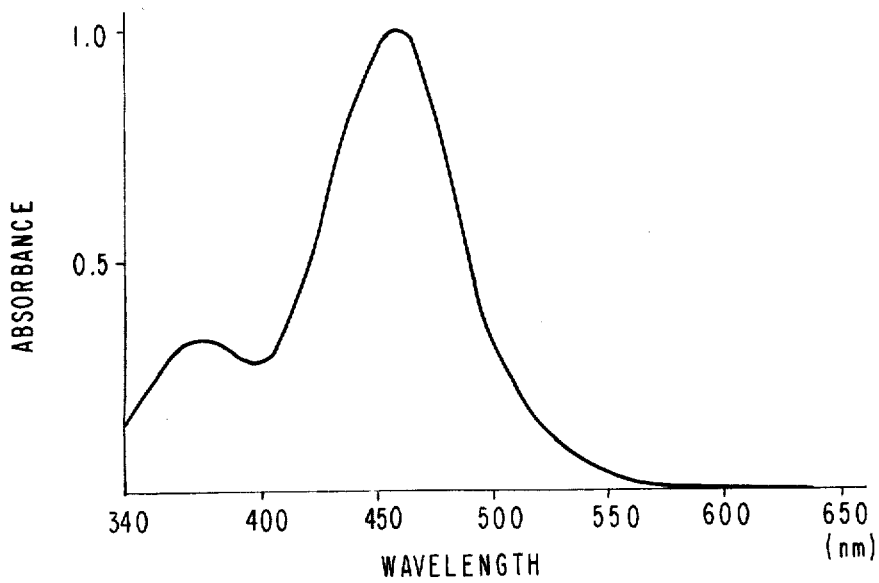
FIG. 4 illustrates the spectral absorption curve of Dye Developer No. 1 after transfer.

FIG. 4 illustrates the result of measurement of the spectral transmittance density for the dye image at the nonexposed area obtained on the image receiving element by a 30 second processing of Photographic Element (I).

Figure 3:
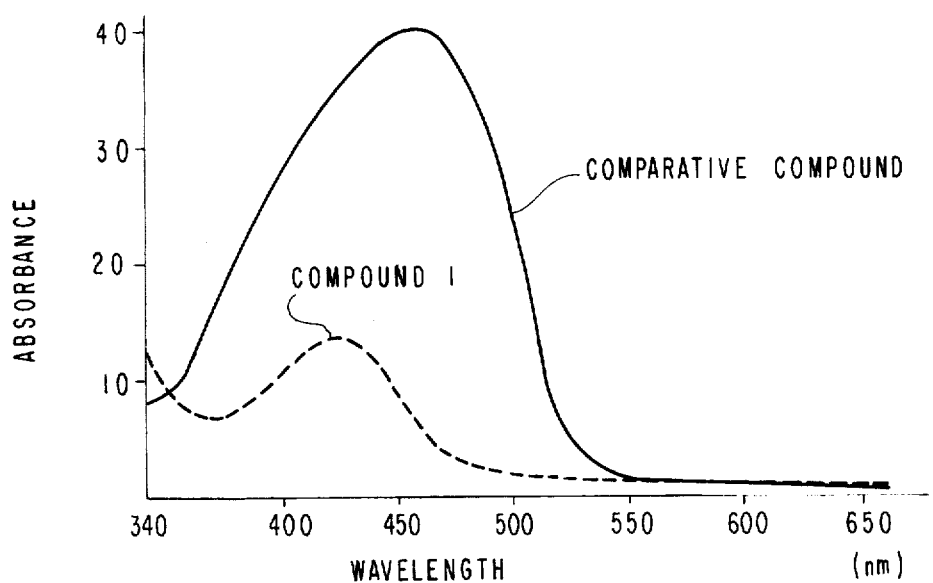
FIG. 3 illustrates the spectral absorption curve of a dye developer layer containing Dye Developer No. 1, and that of another layer for comparison, expressed by absorbence.

Next, the degree of sensitivity reduction which might occur in the case of image exposure from the support side was investigated by carrying out the same development and transfer following image exposure from the side opposite to the support. The degree of sensitivity reduction expressed by $\Delta\log E$ was 0.4 for Photographic Element (I) and 2.4 for Photographic Element (II), respectively, which demonstrates a quite advantageous feature of Photographic Element (I) compared to Photographic Element (II) in this respect. Further, to compare the optical absorption due to the dye developer layer in the photographic element before processing, each of the dye developer layers shown above was coated alone on a cellulose triacetate film having a transparent gelatin subbing layer, and the spectral absorption of the coated sample was measured. The result obtained is shown in FIG. 3.

As is evident from this figure, in the case of Dye Developer No. 1 the absorption shifted to a shorter wavelength region compared with the case of the comparison dye developer, thus averting a reduction in the spectral sensitivity of the blue sensitive emulsion used in combination therewith.

EXAMPLE II

The procedures similar to those in Example I were repeated whereby Dye Developer No. 4 was used in place of Dye Developer No. 1 and 4 parts of N,N-diethyllaurylamide was used in the emulsion formulation for the dye developer in Example I. The other conditions and procedures were exactly the same as in Example I. The absorption in the photographic element prior to processing is shifted hypsochromically and the absorption maximum in the image receiving element was located at 464 m$\mu$. The degree of sensitivity reduction attending the exposure made from the support side, measured by the same method as in Example I, was $-\Delta\log E = 0.4$. Again in this example, the dye developer of the present invention is far better than the reference dye developer ($-\Delta\log E = 2.4$) with respect to this degree of sensitivity reduction.

EXAMPLE III

On a cellulose triacetate film support subbed with gelatin were successively coated the following layers in order.

1. Yellow Dye Developer Layer

A solution prepared by dissolving 1 part of Dye Developer No. 1 with 1 part of N,N-diethyllaurylamide and 4 parts of cyclohexanone was emulsified in an aqueous gelatin solution with the aid of sodium n-dodecylbenzene sulfonate. The dispersion was coated at a rate of 0.8 g/m² of the dye developer, 1.0 g/m² of gelatin, and 0.8 g/m² of N-diethyllaurylamide.

2. Blue Sensitive Emulsion Layer

A blue sensitive silver iodobromide emulsion layer was coated at a coverage of 2.3 g/m² of silver, and 1.7 g/m² of gelatin.

3. Intermediate Layer

A colloidal silver layer with a coverage of 0.3 g/m² of silver and 3.5 g/m² of gelatin.

4. Magenta Dye Developer Layer

A solution prepared by dissolving 1 part of 4-methoxyethoxy-2-[4-(2-hydroquinonylethyl)phenylazo]naphthalene-1-acetate in 1 part of N,N-diethyllaurylamide and 4 parts of cyclohexanone was emulsified in an aqueous gelatin solution with the aid of sodium n-dodecylbenzene sulfonate and this was coated at a coverage of 1.0 g/m² of the dye developer, 1.3 g/m² of gelatin, and 1.0 g/m² of N,N-diethyllaurylamide.

5. Green Sensitive Emulsion Layer

A green sensitive silver iodobromide emulsion layer (iodine content; 2 mole %) containing 3,3',9-triethyl-5,5'-diphenyloxacarbocyanine bromide as a spectral sensitizer, with a coating rate of 1.0 g/m² of silver, and 0.8 g/m² of gelatin.

6. Intermediate Layer

A gelatin layer coated at 3.0 g/m².

7. Cyan Dye Developer Layer

Into 2 parts of N,N-diethyllaurylamide and 4 parts of methylcyclohexanone was dissolved 1 part of 1-(N-carbophenoxy-N-γ-hydroquinonylpropylamino)-4-γ-hydroquinonylpropylamino-5,8-dihydroxy-9,10-anthraquinone. The solution was emulsified in an aqueous gelatin solution with the aid of sodium n-dodecylbenzene sulfonate and the resulting dispersion was coated at a coverage of 0.50 g/m² of the dye developer, 1.2 g/m² of gelatin, and 0.50 g/m² of N,N-diethyllaurylamide.

8. Red Sensitive Emulsion Layer

A red sensitive silver iodobromide (iodine content; 2 mole %) photographic emulsion containing 3,3',9-triethyl-5,5'-dichlorothiacarbocyanine iodide as a spectral sensitizer was coated at a rate of 0.50 g/m² of silver, and 0.37 g/m² of gelatin.

9. Protective Layer

A solution prepared by dissolving 1 part of 4-methylphenylhydroquinone into 1 part of tri-o-cresyl phosphate and 1.5 parts of ethyl acetate was emulsified in an aqueous gelatin solution with the aid of sodium n-dodecylbenzene sulfonate. The dispersion was coated at a rate of 0.45 g/m² of 4'-methylphenylhydroquinone, 1.3 g/m² of gelatin, and 0.45 g/m² of tri-o-cresyl phosphate. Mucochloric acid was added as a hardener.

On the other hand a transparent polyethylene support was coated with the following layers in the following order to prepare an image receiving element.

1. Acid Polymer Layer

A 40 micron thick coating on a dry basis was provided using a 20% methyl ethyl ketone solution of the half butyl ester of maleic anhydride/vinyl methyl ether copolymer having an average molecular weight of about 100,000.

2. Neutralizing Rate Controlling Layer

A solution comprising 1 part of 2-hydroxyethyl methacrylate, 3 parts of acetone and 1 part of water was coated to give a dried thickness of 14 microns.

3. Image Receiving Layer

The same as was described in Example I.

From the support side of the thus prepared photographic element an optical wedge exposure was carried out using red, green and blue light. The following processing liquid was spread at a rate of 1.0 ml/100 cm² of the image receiving element between the exposed photographic element and the image receiving element, for development and transfer.

| Processing Liquid Composition | |
|---|---|
| Water | 100 ml |
| Potassium Hydroxide | 11.2 g |
| Hydroxyethylcellulose | 3.5 g |
| Benzotriazole | 1.5 g |
| N-Phenethyl-α-picolinium Bromide | 2.0 g |
| Titanium Dioxide | 50 g |

In several minutes after the developing processing, the appearance of the red, green blue image from the support side of the image receiving element could be observed without stripping off the image receiving element from the photographic element.

While the invention has been described in detail and with reference to specific embodiments thereof, it will be apparent to one skilled in the art that various changes and modifications can be made therein without departing from the spirit and scope thereof.

What is claimed is:

1. A light-sensitive material for the diffusion transfer process comprising a support having thereon at least one blue-sensitive silver halide emulsion layer and an associated yellow dye developer represented by the following formula:

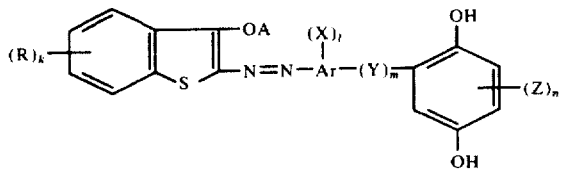

wherein R represents a halogen atom or an alkyl group containing 1 to 4 carbon atoms; $k$ is an integer of from 0 to 4; A represents an acyl group containing 1 to 4 carbon atoms or an alkoxyacyl group containing from 2 to 4 carbon atoms; Ar represents an aromatic nucleus; X represents a halogen atom, an alkyl group, an alkoxy group, an acyl group or an acyloxy group, each containing 1 to 4 carbon atoms $l$ is an integer of from 0 to 4; Y represents an alkylene group containing 1 to 6 carbon atoms or a $+CH_2+_{\overline{p}}Y'+CH_2+_{\overline{q}}$ group wherein Y' represents —O—, —S—, —SO$_2$— or —CONH—; $p$ and $q$ each represents an integer of at least 1 and the sum of $p + q$ is less than 6; $m$ is 0 or 1; Z represents an alkyl group containing 1 to 4 carbon atoms or a halogen atom; and $n$ represents an integer of from 1 to 3.

2. The light-sensitive material as claimed in claim 1, wherein X is in the ortho position with respect to the azo group and wherein $l$ is an integer from 0 to 2.

3. The light-sensitive material as claimed in claim 1, where said yellow dye developer is positioned at the exposure side to said silver halide emulsion layer.

4. The light-sensitive material as claimed in claim 1, wherein the associated yellow dye developer is present in said blue-sensitive silver halide layer.

5. The light-sensitive material as claimed in claim 1, further including a container retaining a processing solution for the light-sensitive material and containing a light-reflecting agent.

6. The light-sensitive material as claimed in claim 5, wherein said light-reflecting agent is titanium dioxide.

7. The light-sensitive material as claimed in claim 1, further including an image-receiving element for the dye images transferred on development of said light-sensitive material, said image-receiving element including a mordant layer with a neutralizing rate controlling layer and a neutralizing layer on the side of said mordant layer opposite said light-sensitive silver halide emulsion layer.

8. The light-sensitive material as claimed in claim 7, wherein said mordant layer contains a mordanting agent having a poly-4-vinylpyridine structure.

9. The light-sensitive material as claimed in claim 1, wherein the silver halide emulsion layer is shielded from light with a light-intercepting agent so that the material can be processed in the light outside a camera.

10. The light-sensitive material as claimed in claim 9, wherein the light-intercepting agent is carbon powder.

11. The light-sensitive material as claimed in claim 1, wherein said yellow dye developer is 3-acetoxy-2-[m-(hydroquinonylmethyl)phenylazo]benzo[b]thiophene.

12. The light-sensitive material as claimed in claim 1, wherein the dye developer is 3-acetoxy-2-[p-(2'-hydroquinonylethyl)phenylazo]benzo[b]thiophene.

13. The light-sensitive material as claimed in claim 1, further including at least one green-sensitive silver halide emulsion layer and an associated magenta dye developer, and at least one red-sensitive silver halide emulsion layer and an associated cyan dye developer.

14. The light-sensitive material as claimed in claim 2, wherein said halogen atom of R represents a chlorine atom or a bromine atom; said alkyl group of R represents a methyl group, an ethyl group, a propyl group, an iso-propyl group, a butyl group, a sec-butyl group or a t-butyl group; said acyl group of A represents an acetyl group, a propionyl group or a butyryl group; said alkoxyacyl group of A represents a methoxyacetyl group; said aromatic nucleus of Ar represents a benzene nucleus or naphthalene nucleus; said halogen atom of X represents a chlorine atom or a bromine atom; said alkyl group of X represents a methyl group, an ethyl group, a propyl group, an iso-propyl group, a butyl group, a sec-butyl group or a t-butyl group; said alkoxy group of X represents a methoxy group, an ethoxy group, a propoxy group, an iso-propoxy group, a butoxy group, a sec-butoxy group or a t-butoxy group; said acyl group of X represents an acetyl group, a propionyl group or a butyryl group; and said acyloxy group of X represents an acetyloxy group, a propionyloxy group or a butyryloxy group.

15. The light-sensitive material as claimed in claim 13, wherein said blue-sensitive silver halide emulsion layer, said green-sensitive silver halide emulsion layer and said red-sensitive silver halide emulsion layer are coated in said order from the side of exposure of said light-sensitive material to light.

16. The light-sensitive material as claimed in claim 15, further including a yellow filter layer between said blue-sensitive silver halide emulsion layer and said green-sensitive silver halide emulsion layer.

17. The light-sensitive material as claimed in claim 15, wherein each of said silver halide emulsion layers is separated from each other by an intermediate layer comprising a hydrophilic polymer.

18. The light-sensitive material as claimed in claim 1, wherein said yellow dye developer is present in an amount from about 0.1 g/m$^2$ to 10 g/m$^2$.

19. The light-sensitive material as claimed in claim 18, wherein said yellow dye developer is present in an amount from 0.3 g/m$^2$ to 4 g/m$^2$.

20. The light-sensitive material as claimed in claim 1, wherein the coating amount of said silver halide emulsion ranges from about 0.1 g/m$^2$ to 10 g/m$^2$ of said silver halide, as silver.

21. The light-sensitive material as claimed in claim 20, wherein said coating amount ranges from 0.3 g/m$^2$ to 4 g/m$^2$ of said silver halide, as silver.

22. The light-sensitive material as claimed in claim 13, wherein the yellow dye developer is present in said blue-sensitive silver halide emulsion layer, the magenta dye developer is present in said green-sensitive silver halide emulsion layer and the cyan dye developer is present in said red-sensitive silver halide emulsion layer.

* * * * *